United States Patent [19]
Lacruche et al.

[11] Patent Number: 5,315,986
[45] Date of Patent: May 31, 1994

[54] APPARATUS FOR REAL-TIME TRACKING AND IMAGING OF OBJECTS WITHIN THE BODY OF A MAMMAL

[75] Inventors: Bernard Lacruche, Lyons; Dominique Cathignol, Genas; Francois Lacoste, Lyons, all of France

[73] Assignees: Technomed International; Inserm (Institut National de la Recherche Medicale), both of Paris, France

[21] Appl. No.: 675,509

[22] Filed: Mar. 27, 1991

Related U.S. Application Data

[63] Continuation-in-part of Ser. No. 405,358, Aug. 28, 1989, abandoned.

[30] Foreign Application Priority Data

Aug. 31, 1988 [FR] France ............................ 88 11414

[51] Int. Cl.$^5$ ............................................. A61B 17/22
[52] U.S. Cl. ...................................... 69/4; 128/660.03
[58] Field of Search ........ 128/24 AA, 24 EL, 660.01, 128/660.03, 662.03, 663.01

[56] References Cited

U.S. PATENT DOCUMENTS

| 3,942,531 | 3/1976 | Hoff et al. | |
| 4,399,822 | 8/1983 | Theumer | |
| 4,444,197 | 4/1984 | Koyano et al. | |
| 4,669,483 | 6/1987 | Hepp et al. | 128/660.03 |
| 4,771,787 | 9/1988 | Wurster et al. | |
| 4,821,729 | 4/1989 | Makofski et al. | 128/660.03 |
| 4,821,730 | 4/1989 | Wurster et al. | 128/660.03 |
| 4,928,672 | 5/1990 | Grasser et al. | 128/24 EL |
| 4,984,575 | 1/1991 | Uchiyama et al. | 128/660.03 |
| 5,058,590 | 10/1991 | Wurster | 128/660.03 |
| 5,078,124 | 1/1992 | Viebach et al. | 128/660.03 |
| 5,078,144 | 1/1992 | Sekino et al. | 128/660.03 |
| 5,095,908 | 3/1992 | Belikan et al. | 128/660.03 |

FOREIGN PATENT DOCUMENTS

WO87/01927 4/1987 World Int. Prop. O.

Primary Examiner—Lee S. Cohen
Assistant Examiner—Krista M. Pfaffle
Attorney, Agent, or Firm—Cohen, Pontani, Lieberman, Pavane

[57] ABSTRACT

The invention relates to an apparatus for a real-time tracking and imaging of objects. The apparatus comprises of a real-time image forming device, a device for coupling the image forming device with a wave generator generating waves adapted to effect appropriate treatment of said object directed towards a target focus, wherein the coupling device includes a device for displacing the image forming device relative to said target focus. The invention offers the advantage of great positional freedom for the image forming device, enhanced resolution and safe observation of objects within the body of a mammal, and in particular a human being. The object is in particular selected from a concretion, a bone or a tumor, notably a cancerous tumor.

16 Claims, 3 Drawing Sheets

APPARATUS FOR REAL-TIME TRACKING AND IMAGING OF OBJECTS WITHIN THE BODY OF A MAMMAL

This application is a continuation in part of application Ser. No. 07/405,358 of Aug. 28, 1989 now abandoned.

BACKGROUND OF THE INVENTION

1. Field of the Invention

The present invention essentially relates to an apparatus for real-time tracking—i.e. for detecting, locating and tracking onto—and imaging concretions, within the body of a mammal.

Concretions occur naturally in cavities of mammals, especially human beings. As these concretions form, they rapidly lead to an obstruction of the natural passages, inevitably causing serious physiological disorders that can endanger the life of the mammal concerned.

2. Prior art

In recent years, various devices have been proposed for destroying concretions into small-size fragments that can be evacuated by the natural passages. These devices operate from outside the body using pressure wave generators directed towards the concretion. For example, U.S. Pat. No. 2,559,227 (RIEBER) discloses a pressure wave generator comprising a truncated ellipsoidal reflector in which pressure waves are generated by discharge or an electric arc between two concurrent electrodes at the first focus of the ellipsoid so as to destroy a target, e.g. consisting of a concretion, located at the second focus of the ellipsoid.

In practice, there occurs a serious problem concerning the correct positioning of the target to be destroyed exactly on the second focus of the ellipsoid.

This calls for a detection and exact determination of the position of the target to be destroyed, e.g. a concretion, such as a kidney stone or a biliary concretion.

Various exploratory probes are available for the detection and positioning of such targets, including X-rays or, as is more usually preferred, ultrasounds using ultrasonic transducers.

For example, U.S. Pat. No. 4,444,197 discloses a probe type exploratory apparatus for diagnosis by ultrasound that uses two articulated arms. A similar description is contained in U.S. Pat. No. 4,399,822.

U.S. Pat. No. 4,669,483 discloses a device for spatially positioning an exploratory probe.

The applicants have also proposed a device for spatially positioning an exploratory probe, in copending U.S. patent application Ser. No. 112,434.

However, it turns out in practice that it is necessary for the practitioner to be able to control in real time the position of the concretion and to keep track of its fragmentation during the treatment.

Various solutions have already been put forward for monitoring the position of the concretion and keeping track of its fragmentation during the treatment.

For example, WO-A-8701927 discloses an apparatus for detecting stone fragments, in association with a lithotriper. The lithotripter has a spherical focusing cup serving as a power transducer, and the detection apparatus includes an auxiliary, sectorially-scanned transducer fixed to the center of the cup and connected to an echograph. The apparatus has an auxiliary exciter for the power transducer, generating pulses at a rate of a few hertz and at low power compared with the firing pulses. During the low power pulses, the echograph receiver is operatively connected to an auxiliary cathode-ray tube that produces an A-type echograph image for detecting the stone fragments.

An equivalent disclosure is made in U.S. Pat. No. 4,771,787 and U.S. Pat. No. 4,821,730.

In both devices, the A or B type scanner or transducer is located coaxially to the generator producing pressure waves focused on the target-focus and has to be adjusted on the concretion to be destroyed.

By virtue of the coaxial position of the transducer or A or B type scanner, it is possible to continuously view the concretion when the latter is made to coincide with the focus of the pressure wave generator cup.

However, these devices are limited in their scope for spatial positioning, even if they are mounted so as to revolve around their own axis and to be translatable along the symmetry axis of the pressure wave generator.

Yet the possibility of spatially displacing the concretion locating and imaging apparatus appears necessary in order to keep track of any displacement of the concretion, as well as of the fragments produced in the course of treatment. This is essential to avoid emitting pressure waves that would miss the concretion. The operator should thus be able to stop immediately the emission of pressure waves to proceed to a new locating step.

This is why U.S. Pat. No. 4,663,483 teaches an ultrasonic locating device located at the end of a complex mechanical structure for the spatial detection of the concretion, to determine its coordinates and subsequently to bring the target-focus of the pressure wave generator into coincidence with the concretion to be destroyed, through the use of a complex processing system.

Since the above locating device is somewhat immobilized while the concretion is set into coincidence with the target focus of the pressure wave generator, it cannot be used by the practitioner for real-time observation of the concretion.

This is why it can be noted that the document proposes the inclusion of a complementary real-time imaging device formed by an ultrasonic transducer or scanner fixed to a peripheral point of the pressure wave generator, which can be moved only about the axis of the focusing chamber. This ultrasonic tranducer or scanner has a higher resolution than the displaceable ultrasonic device and allows viewing of the destruction of the concretion (see page 13, lines 6 to 16). Such a limited motion is not sufficient to obtain the best resolution nor monitor wide regions in the body.

Such an auxiliary ultrasound or scanner device has also been proposed in document EP-A-0 265 742. Here, the two ultrasonic locating devices are located at right angles so as to provide viewing planes that are also at right angles. The position of these ultrasonic transducers or scanners is also fixed with respect to the generator.

But, as has already been mentioned above, concretions or their fragments are relatively frequently displaced in the course of a treatment.

This is particularly true for the treatment of biliary concretions. Indeed, these concretions move much more than kidney stones since they have considerably more space within which to move and can easily escape from the target-focus after recoiling from the shock waves, or as a result of patient movements. Furthermore, patients' respiratory movements are considerable at the level of vesicle, given that the vesicle and the liver are both in direct contact with the diaphragm. Thus, there is a strong likelihood in this case that a non-negligible part of the shock or pressure waves does not reach the concretion, owing to the respiratory movements.

All the previously proposed solutions, using a fixed position of the auxiliary ultrasonic locating device or scanner, or using limited axial or two-dimensional displacement relative to the pressure wave generator, have the major drawback of granting little freedom for positioning the locating device making it (in practice) very difficult (if not impossible in at least some instances) to locate and view the concretions effectively in real time, especially in the case of biliary concretions, during the course of the treatments.

SUMMARY OF THE INVENTION WITH OBJECTS

The present invention therefore aims to solve the new technical problem consisting in providing a solution for controlling and viewing objects within the body of a mammal, in particular a human being, such as concretions or their fragments in real time, irrespective of their displacement during the course of the treatment.

Another aim of the present invention is to solve the new technical problem consisting in providing a solution for monitoring the position of objects within the body of a mammal, in real time and to keep track of the objects during the treatment, practically without limiting the freedom of positioning of the device for real-time tracking and positioning of the objects, and thus enabling the maximum acoustic window to be sought.

Yet another aim of the present invention is to solve the new technical problem consisting in providing a solution for detecting and viewing objects within the body of a mammal and their fragments in real time in the course of the treatment, independently of their displacements while accommodating for the displacements of the tracking and spotting device associated to the generator, thereby allowing observation of the target-focus zone, offering the decisive advantage of being easily accessible to the operator in the event of a replacement, and allowing the use of different types of ultrasonic transducers or scanners.

Further, the aim of the present invention is to solve the new technical problem consisting in providing a solution for detecting and viewing objects within the body of a mammal in real time by means of a highly manoeuvrable apparatus, resulting in a time saving and a better control of the treatment, and hence in an overall improvement in the efficiency of the treatment.

Still further, the aim of the present invention is to solve the new technical problem consisting in providing a solution for detecting and viewing objects within the body of a mammal in real time with the possibility of respiratory synchronization by virtue of the possibility given to the practitioner of determining at which instant during the respiratory cycle the concretion returns to the center of the focal point, normaly highlighted by a cross on the echograph image.

The main aim of the present invention is to solve the new technical problem consisting in providing a solution for permitting use of a single image forming means to track and image an object present within the body of the mammal, in particular the human being, in real time.

Another further main object of that invention is to solve the new technical problem consisting to ensure a virtually limitless choice of acoustic windows which in turn allows optimal performance of the image forming means and, the same problem, ensures easy operation.

Finally, another main aim of the present invention is to provide a solution permitting a displacement of the image forming means with regard to the object to be followed in real time, such as a concretion, a bone or a tumor, while permitting measuring any displacement value of the image forming means, in particular with regard to a wave generator generating waves directed towards a target focus zone for appropriate treatment of said object, while using a single image forming means.

All the above technical problems are solved for the first time by the present invention in an extremely simple, reliable and economical manner that is workable on an industrial scale.

Thus, according to a first aspect, the present invention provides an apparatus for real-time tracking and imaging of an object present within the body of a mammal, in particular a human being, said object being in particular selected from a concretion, a bone or a tumor, using a wave generator generating waves adapted to perform appropriate treatment of said object, directed towards a target focus zone put into coincidence with said object, comprising image forming means forming a real time image of said object for real-time observation of the latter, and coupling means for coupling said image forming means with said wave generator, said coupling means comprising displacing means providing displacement of the image forming means in a displacement plane coinciding with a symmetry plane of said generator including said target focus zone and including a longitudinal axis of said image forming means, said image forming means being coupled to said displacing means whereby said image forming means is movable in displacement in said displacement plane relative to said target focus zone.

According to another advantageous embodiment of the present invention, said coupling means are adapted to permanently have the longitudinal axis of said image forming means passing through said target focus zone.

According to another advantageous embodiment of the present invention, said displacement means comprise translation means providing translation along said longitudinal axis of said image forming means passing through said target focus zone. Accordingly, the translation means constitute axial translation means for providing axial translation along said longitudinal axis of said image forming means passing through said target focus zone, thereby providing positioning said image forming means closer or farther from the target focus zone.

According to another advantageous embodiment of the present invention, said displacement means comprise rotation means providing rotation within said displacement plane around said target focus zone.

According to a particular embodiment, said rotation means comprise an arcuate member having, as geometrical center, said target focus zone, linked to said wave generator provided with a movable member supporting said image forming means and mounted displaceable on said arcuate member to provide the displacement movement of said movable member with regard to said arcuate member constituting a rotation movement around said target focus zone in said displacement plane and thereby of said image forming means supported by said movable member.

According to a specific embodiment, said object is a concretion. According to a another specific embodiment, said object is a bone or bone zone for instance a bone structure which has to be treated by waves. According to a further specific embodiment, said object is a tumor, in particular a cancerous tumor within any part of the body of the mammal, in particular a human being.

According to another specific embodiment, said wave generator is a pressure wave generator generating pressure waves directed towards a target focus zone put into coincidence with said object.

According to a particularly preferred embodiment, said pressure wave generator comprises an ellipsoidal reflector having an inner focus where are generated the pressure waves and an outer-focus where are directed said pressure waves generated at the inner focus. The ellipsoidal reflector is preferably filled with a liquid coupling medium, in particular water or a very electro-conductive liquid, notably salted water.

According to another specific embodiment, said displacement means comprise first displacement means for providing displacement in a first given direction in said displacement plane, and second displacement means providing displacement in a second direction in said displacement plane, in particular substantially perpendicularly to said first given direction.

According to another specific embodiment of the present invention, said displacement means comprise a support that is displaceably mounted on the external periphery of said wave generator.

According to another particular embodiment of the invention, said image forming means are rotatably mounted with the respect to said coupling means. In particular, said coupling means comprise a through opening inside which said image forming means are rotatably mounted.

According to another specific embodiment, said coupling means comprise a rail type coupling system, in particular of the monorail type.

According to a specific characteristic, said coupling means comprise a shoulder section displaceably mounted on the upper edge of said wave generator.

According to another specific embodiment, said pressure wave generator is an ultrasonic type shock wave generator, for instance with a spherical cup, providing natural focusing of the ultrasonic waves to the geometrical focus center of the spherical cup constituting the target focus zone.

According to another specific embodiment of the invention, said image forming means comprise a least one ultrasonic transducer or scanner, preferably of the B type, operating in real time.

According to a second aspect, the present invention also provides a wave generating apparatus for extracorporeal treatment of an object within the body of a mammal and in particular a human being, wherein said apparatus comprises an apparatus for real-time tracking and imaging as hereinabove defined. This wave generating apparatus is preferably a pressure wave generating apparatus, and notably a lithotripter. Specifically, the lithotripter can be a hydraulic type lithotripter that generates hydraulic shock waves, or an ultrasonic lithotripter that generates ultrasonic waves.

Accordingly, it can be seen that the invention offers all above mentioned decisive technical advantages.

BRIEF DESCRIPTION OF THE DRAWINGS

Other aims, characteristics and advantages of the invention shall be brought out more clearly in the light of the following description made with reference to the appended drawings depicting a presently preferred embodiment of the invention, given merely as an example, and which therefore in no way restrict the scope of the invention. In the drawings.

DETAILED DESCRIPTION OF THE PREFERRED EMBODIMENTS

Figure 1:
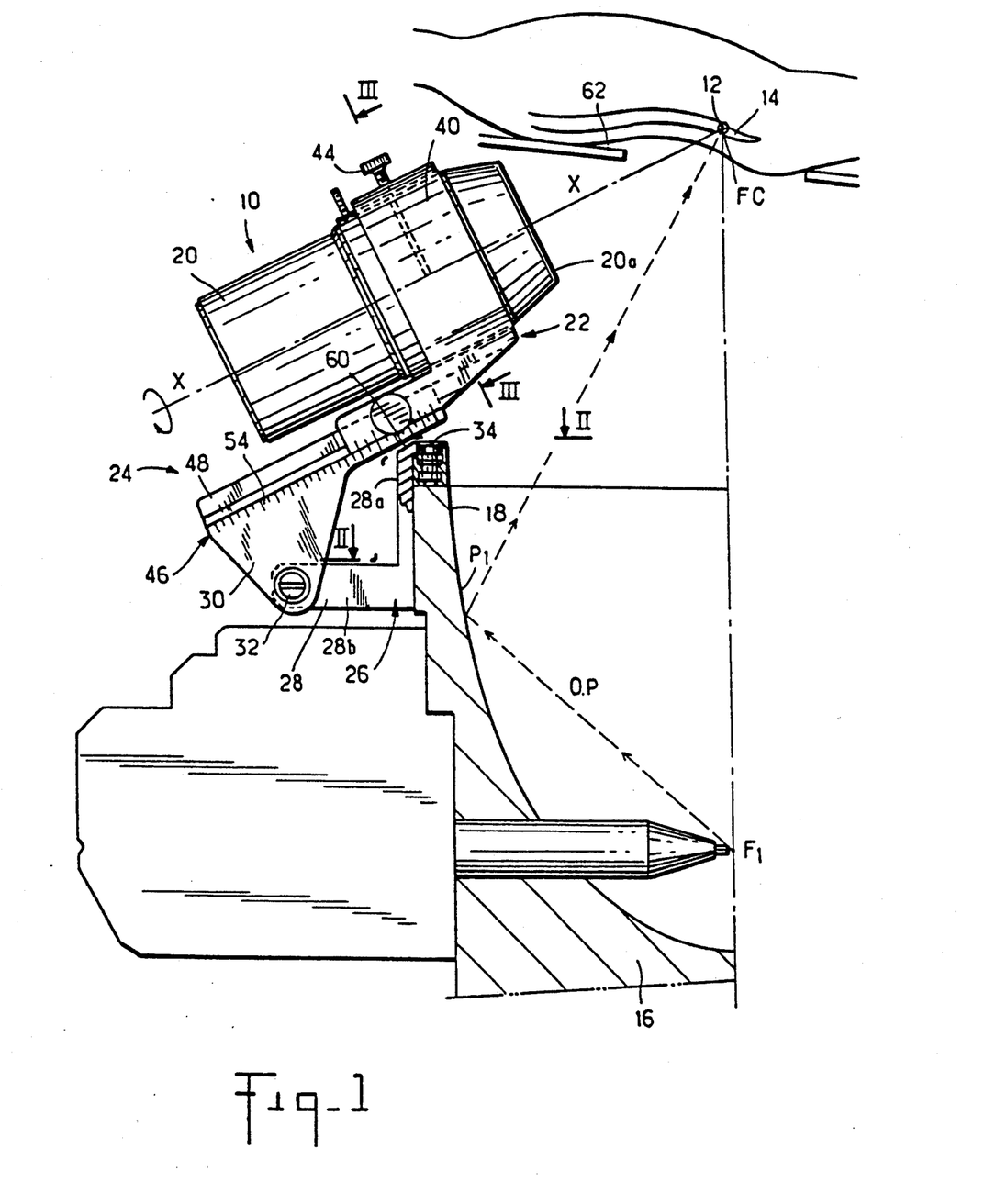
FIG. 1 is an axial half cross-sectional view along the cross-section line I—I of FIG. 2 of a pressure wave generating apparatus, in this case formed by a hydraulic lithotripter having an ellipsoidal reflector of the type described by RIEBER in patent U.S. Pat. No. 2,559,927 or in U.S. Pat. No. 3,942,531, fitted with an apparatus for real-time tracking and imaging according to the invention.
Figure 2:
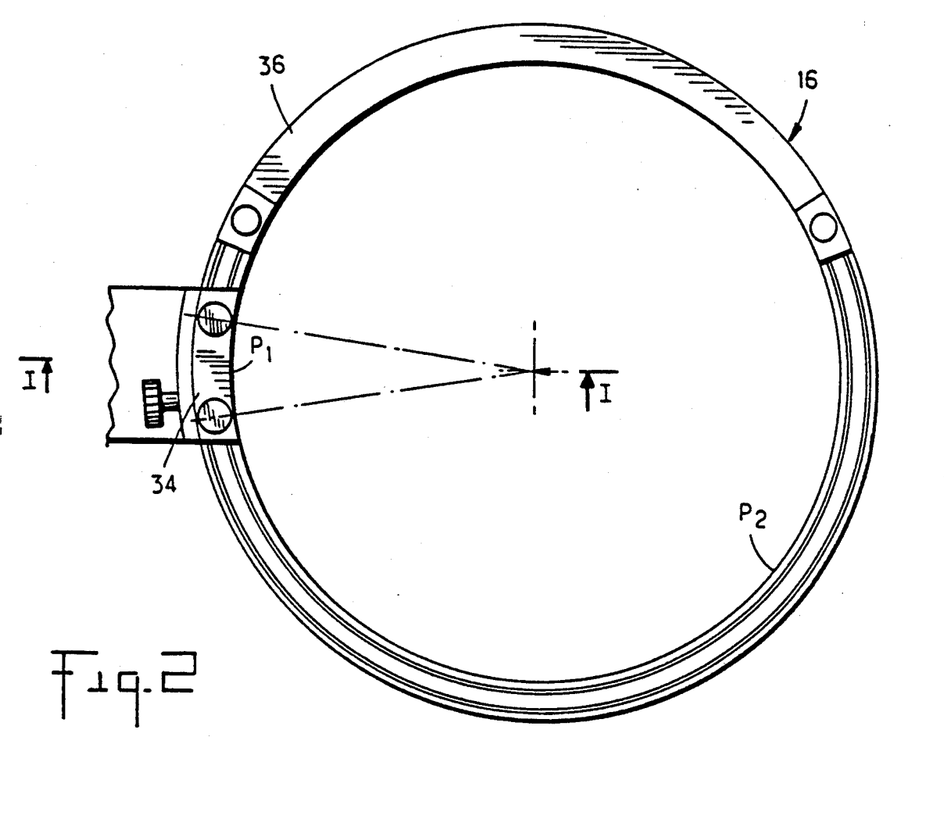
FIG. 2 is a top view according to arrow II of FIG. 1, revealing in full the top of the reflector shown in axial half cross section in FIG. 1.
Figure 3:
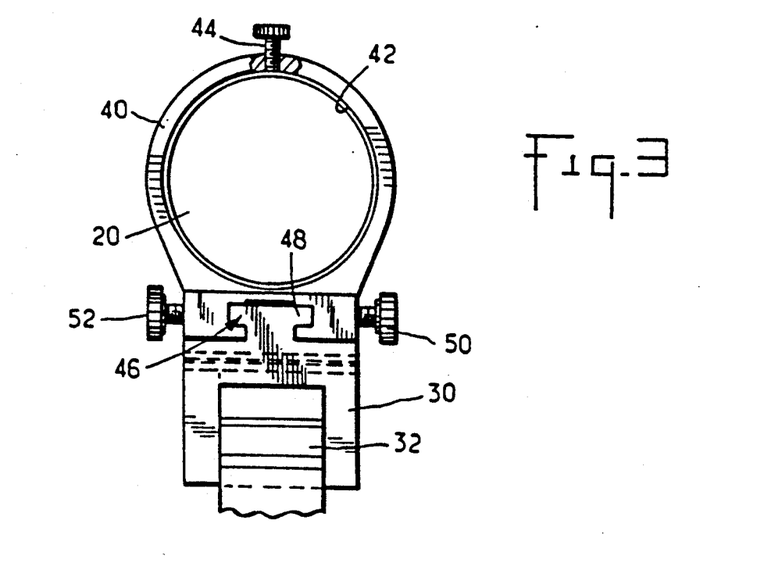
FIG. 3 is a sectional view along the cross-section III—III of FIG. 1.

With reference to FIGS. 1 to 3, there is shown an apparatus according to the invention generally designated by reference number 10, for real-time tracking an imaging of an object 12 within the body of a mammal, in this particular case a human being. This object can be a concretion as shown in the drawings, or a bone or in particular a bone structure, or a tumor, in particular cancerous tumors. There is also presented a wave generator generally designated by the reference number 16. This wave generator 16 is capable of generating waves adapted to perform appropriate treatment of said object and to direct said waves towards a target focus zone F.C. that is put into coincidence with said object 12, that is clearly apparent in FIG. 1.

The real time object tracking and imaging apparatus 10 comprises image forming means 20 capable of forming a real time image of the object 12. Such image forming means are well known and preferably according to the invention include an ultrasonic transducer or scanner, in particular a B type scanner, also known as a sectorial scanning ultrasonic probe. Such image forming means 20 are well known to the man skilled in the art of ultrasounds or echography and will not be described here in more detail.

The apparatus 10 also comprises coupling means generally designated by reference number 22, for coupling the image forming means 20 with the wave generator 16. Here, the wave generator 16 is shown as constituting a pressure wave generator here comprising a truncated ellipsoidal reflector 18 having an inner focus $F_1$ and an outer focus FC. In that case, the pressure waves O.P. generated at the inner focus $F_1$ are focused by the inner surface of the ellipsoidal reflector 18 to the other focus FC constituting therefore the target focus zone where the object 12 is put into coincidence to be treated by said waves as it is well known to anybody skilled in the art.

According to the invention, said coupling means 22 comprise displacing means generally designated by reference number 24 for displacing the image forming means 20 in a displacement plane coinciding with a symmetry plane of said generator 16 including said target focus zone FC and including a longitudinal axis X—X of said image forming means 20, namely here the plane defined by the paper in FIG. 1. Said image forming means 20 are coupled to the displacing means 24 whereby the image forming means 20 are movable in displacement in said displacement plane relative to the target focus zone FC. According to a particular preferred embodiment, the coupling means 22 are adapted to permanently have the longitudinal axis X—X of the image forming means, passing through the target focus zone FC, as clearly shown on FIG. 1.

According to a particular embodiment shown on FIGS. 1 to 3, the displacing means 24 are adapted to provide a displacement at the periphery of the wave generator 16 around the target focus zone FC, e.g. from one external peripheral point $P_1$ to another external peripheral point $P_2$ (FIG. 2).

According to a specific embodiment, the image forming means 20 are connected with a support 26 that is displaceably mounted on the external periphery of the wave generator 16, as can be clearly seen and understood from FIGS. 1 to 3.

According to a particular embodiment of the invention, shown in FIGS. 1 to 3, the support 26 includes a fixed part 28 and a rotatable part 30, which are mutually articulated by an articulation axle 32 located substantially perpendicularly to the symmetry plane of the generator 16 containing the longitudinal axis X—X of the image forming means 20, which is the cross-section of FIG. 1. Thus, since the generator 16 is generally located so that the focal axis F1-FC is vertical, the articulation axle 32 is located substantially horizontally so that the rotatable part 30 rotates in a vertical plane, in the plane defined by the paper in FIG. 1.

According to another specific characteristic, the support element 26 has a shoulder section 34 which in this case is naturally connected to the fixed part 28 and is slidably mounted on the upper edge 36, clearly visible in FIG. 2, of the generator 16 while being connected to the latter. As an example, this displacement can be implemented by a system of ball bearings, or a rail system, both of which are well known in the art.

According to a preferred embodiment, the support 26 is mounted so as to be displaceable relative to the generator 16 over a large displacement angle, preferably greater than 90°, and, better still, greater than 360°.

According to a specific embodiment, the fixed part 28 of the support 26 is mounted so as to be displaceable, e.g. by its shoulder section 34, over the upper edge 36 of the generator 16, by means of a rail-type coupling system, preferably a monorail.

According to a particular embodiment, said displacing means 24 comprise translation means 46 (FIG. 3) providing translation along said longitudinal axis X—X of said image forming means 20 passing through said target focus zone FC. These translations means 46 can comprise an intermediate element 40 having a through opening 42 in which the image forming means 20 are rotatably mounted. In general, the image forming means 20 are held in a sealed housing having a substantially cylindrical shape, as depicted in FIGS. 1 and 3. Locking means 44 such as a screw can naturally be provided at an arbitrary location.

The intermediate element 40 is mounted so as to be displaceable in translation on a translation guiding member 48, for instance due to the provision of a rail type coupling system provided at the bottom part of the intermediate element 40 and at the upper part of part 30, defining a monorail 48. Part 30 is here a rotatable part, which is not compulsory.

According to another embodiment, parts 28 and 30 can be merged in a single part, thereby having by construction the translation movement provided by the guiding member 48 providing a displacement of the image forming means 20, according to axis X—X passing permanently through target focus zone FC, thereby viewing permanently the target focus zone FC. The monorail 48 coupling system and the translation means 46 are well known in mechanical engineering and should therefore not be described in detail.

The invention offers the advantage of allowing very precise translational displacement and of being very easily lockable in any position by locking means 50, 52, such as screws.

There can be provided, on at least one apparent lateral face of part 30, displacement measuring means 54 for measuring the distance of displacement of displacing means, such as a roller on which is marked the position of the image forming means 20 at which the target focus FC appears at the center of the ecograph image. The displacement measuring means 54 preferably also indicates the distance separating the front end 20a of the image forming means 20 from the target focus FC.

According to another specific embodiment of the invention, the cross-section of the fixed part 28 of the support 26 has the shape of an "L" abutting the generator 16, as is clearly visible from FIG. 1, with the vertical bar 28a of the "L" bearing the shoulder section 34, and the horizontal bar 28b bearing the rotation axle 32 at its free end. Preferably, the shape of the rotatable part 30 is such that, with the above configuration, the rotatable part 30 presents its face bearing the monorail 48 when in a rest position, as shown in FIG. 1, that is resting on the upper end of the fixed part 28, along a direction subtending an angle substantially equal to a 45° with respect to the horizontal. Consequently, the longitudinal axis X—X of the image forming means 20 are also disposed at an angle of approximately 45°, which is a preferential angle for the acoustic window. For an easier support of the rotatable part 30 on the fixed part 28, and in particular the upper edge of the L-shaped fixed part 28, there can be provided a flattened portion 60 at the junction between the shoulder section 34 and the vertical bar 28a. Preferably, the rotation axle 32 is devised in such a way that it is possible to lock the rotatable part 30 in any vertical position relative to the fixed part, by use of appropriate locking means well known to the man of the art, such as screws (not shown).

Figure 4:
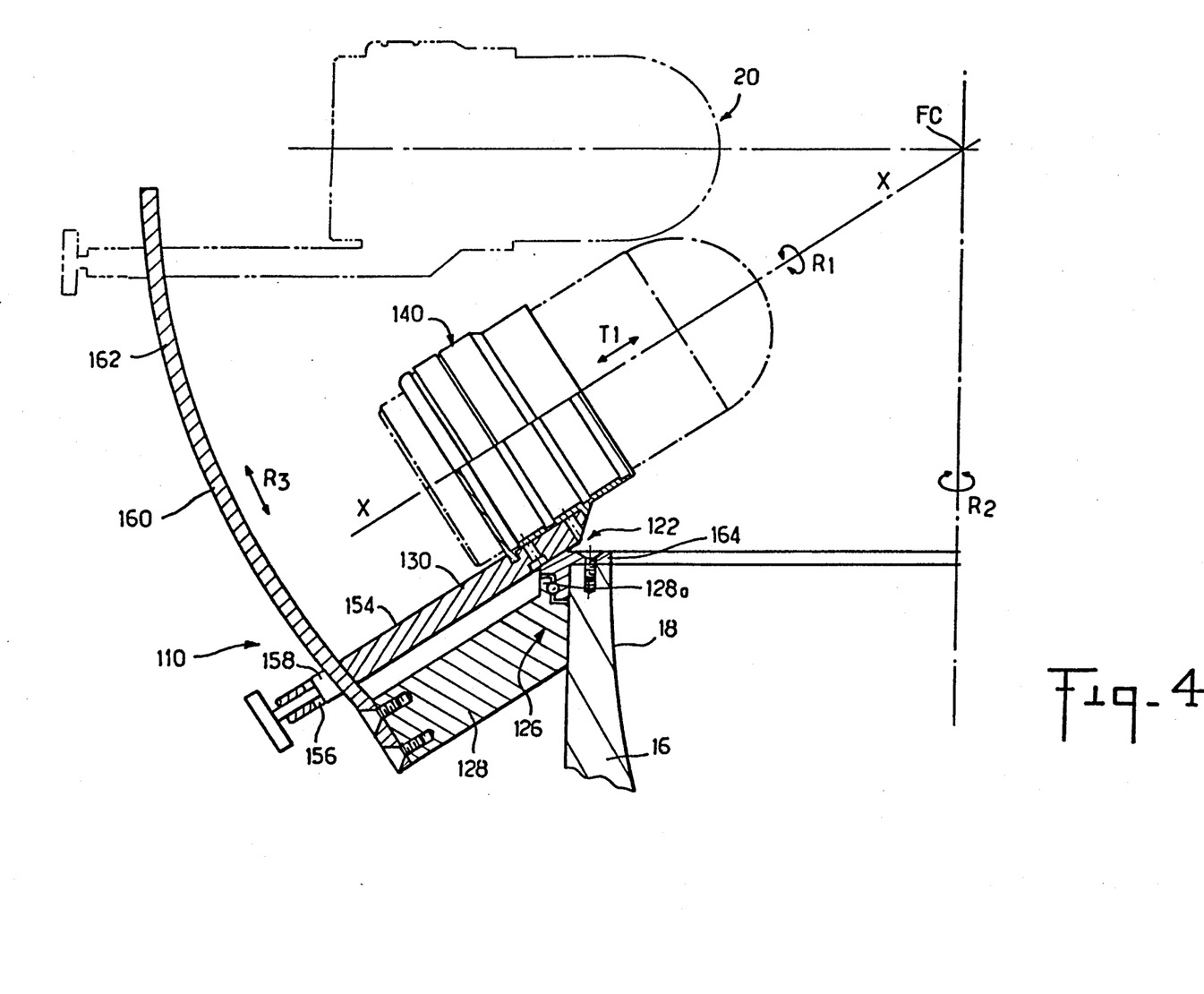
FIG. 4 is a axial half cross-sectional view similar to that of FIG. 1 showing a second embodiment of an apparatus for real-time tracking and imaging according to the invention.

In FIG. 4, the second embodiment of real time tracking and imaging apparatus according to that invention has been shown. The elements having the same function are referenced with the same reference number but increased by one hundred, and therefore, the real time tracking and imaging apparatus is here referenced 110. The wave generator bears the same reference 16 and the inner surface having the shape of a truncated ellipsoidal reflector being referenced 18 as in FIG. 1. The image forming means 20 bears the same reference number. The coupling means bear here the reference number 122. These coupling means 122 comprise respectively from the image forming means 20 to the wave generator 16 the following elements: an image forming means receiving member 140 having a through opening like the element 40 in FIG. 1 and allowing a rotation of the image forming means 20 about its longitudinal axis X—X as shown by a rotational axis $R_1$. The bottom part of receiving member 140 is adapted to permit translation substantially parallely to longitudinal axis X—X as shown by arrows $T_1$ on the translation guiding member 130 analogous to member 30 of FIG. 1. Translation guiding member 130 can also include a translation measuring means 154 like measuring means 54. On FIG. 4, the most advanced translated position is shown and the most rear translated position is quite understandable for anybody skilled in the art.

According to this second invention embodiment, the translation guiding member 130 can be displayed in rotation according to rotation arrow $R_3$ around target focus point FC. This is here ensured for instance by the provision of an arcuate member 160 having as geometrical center said target focus point FC. Said arcuate member 160 is linked to said wave generator 16 according to other elements which will be described hereinafter. Translation guiding member 130 constitutes a movable member mounted displaceable on said arcuate member 160 by having in a part thereof an opening 156 and a locking element 158 allowing locking of the translation guiding member 130 at any position on the arcuate member 160 as clearly understandable for anybody skilled in the art from the two exemplary positions shown on FIG. 4. Also displacement measuring means 162 can be provided on arcuate member 160 to measure the value of translation or preferably the value of rotation of the translation guiding member 130 around the target focus point FC.

Now arcuate member 160 is linked to another displacing means 126 by an intermediate element 128 analogous to element 28 FIG. 1, which provide a rotational movement around target focus point FC according to rotational direction $R_2$, which is perpendicular to the paper plane also called the displacement plane. This rotational movement $R_2$ is provided by displacement at the periphery of the wave generator 16. The complementary displacement means 126 can comprise a rotational part 128A sliding and rotating on a fixed part 164, notably by the provision between the fixed part 164 and rotatable part 128A of a ball-rolling mechanism well known to anyone skilled in the art.

In view of this, this second invention embodiment of FIG. 4 provides a rotational movement of the image forming means 20 according to arrow $R_1$, a translation movement of the image forming means 20 according to translation direction $T_1$, a rotational movement around FC according to rotational direction $R_3$, within the displacement plane defined by the paper plane of FIG. 4 and finally a rotational movement according rotational direction $R_2$ around and perpendicularly to the focus axis F1-FC. Rotational direction $R_2$ is perpendicular to the displacement plane containing focus axis F1-FC.

Therefore, with the real time tracking and imaging apparatus according to the present invention and as described above, there is provided a great freedom in the positioning of the image forming means 20. This enables the optimum acoustic window to be selected to obtain a high-quality echographic image. This makes it possible in virtually all cases to keep track of the object and notably the fragmentation of the concretions, in an accurate manner. Furthermore, the structural characteristics of the invention apparatus grants exceptional manoeuvrability to the image forming means 20, giving a virtually limitless choice of acoustic windows, which in turn allows the image forming means 20—such as a B type scanner or echograph—to operate at maximum performance, while ensuring optimum ease of use.

Also, it is extremely easy to change the image forming means 20 for other image forming means, e.g. having different emission frequencies for easier detection of objects such as concretions, bones and tumors that may otherwise be too deep or too superficial.

Further, the invention makes it extremely easy to view the zone in which passes the pressure waves emitted by the pressure wave generator 16. It is possible to view the complete passage zone by making the image forming means 20 to rotate around the longitudinal axis X—X.

The apparatus according to the invention provides the operator with continuous information on the treatment, notably fragmentation process. Should the object leave the focal zone FC, the operator becomes immediately informed. He/she then knows that the subsequently emitted pressure waves will be without effect since they will not reach the object 12.

By interrupting the emission of pressure waves and re-positioning the object on the focal point, the operator ensures that all the emitted pressure waves contribute towards treatment of the object.

As a result, the number of pressure waves used in a treatment is theoretically reduced, since useless shots are eliminated. This leads to a time saving and a better management of the treatment time. The object 12 is always relocalized at the right moment.

The invention also grants the possibility of synchronization with respiratory movements.

It has been known for a long time that respiratory movements cause considerable displacement of objects, notably concretions. Thus, if the operator judges it necessary, he/she can use the real time viewing possibility available at all times to control the emission of a pressure wave when, in the course of a respiratory cycle, the object, in particular a concretion, returns to the center of the focal point FC, which is usually highlighted by a cross on the echographic image.

The invention furthermore makes it possible to position the image forming means 20 in contact against the patient's body, which enables the resolution to be improved (it should be noted that in FIG. 1, the position of the table 62 supporting the patient is deliberately incorrect to help understand the drawing showing the body of the patient which is not shown to scale; normally, this position is considerably shifted away and thus no obstacle can hinder the displacement of means 10, especially along the direction X—X or in the vertical plane).

The apparatus according to the invention can be fitted to any type of wave generator, be it a generator for hydraulic lithotropsy, especially of the type having an ellipsoidal reflector, as shown in FIGS. 1 to 4, or an ultrasonic generator, e.g. having a spherical cup fitted with a mosaic of piezoelectric transducers.

To facilitate the setting into rotation of the image forming means 20 relative to the intermediate element 40, it is possible to adopt the structure described and shown with reference to FIG. 5 of copending U.S. patent application Ser. No. 117,434 from the present assignees.

It is thus clear that many variants and modifications of the apparatus according to the invention are possible without departing from the scope of the latter. The invention thus comprises all the means forming technical equivalents of the means described, as well as their various combinations.

It should be noted that the structures depicted in FIGS. 1 to 4 form an integral part of the invention, and hence an integral part of the description. The invention also covers any new structure resulting from the above description, including the drawings, over the prior art.

What is claimed is:

1. An apparatus for real-time tracking and imaging of an object present within the body of a mammal, said apparatus comprising:

a wave generator generating waves adapted to effect appropriate treatment of said object and directed towards a target-focus zone put into coincidence with said object;

image forming means forming a real-time image of said object for real-time observation of the latter; and means for connecting said image forming means with said wave generator, said connecting means including means for displacing said image forming means in a displacement plane coinciding with a symmetry plane of said generator including said target-focus zone and including a longitudinal axis of said image forming means, said image forming means being coupled to said displacing means whereby said image forming means is movable in said displacement plane relative to said target-focus zone, wherein said displacing means comprises means for rotating said image forming means within said displacement plane around said target-focus zone, wherein said means for rotating comprise an arcuate member connected to said wave generator and having as a geometrical center said target-focus zone, and a movable member connected to said image forming means and mounted for movement on said arcuate member.

2. The apparatus of claim 1, wherein the connecting means permanently aligns the longitudinal axis of said image forming means with said target-focus zone of said wave generator.

3. The apparatus of claim 1, wherein said displacing means comprises means for moving said image forming means in translation along said longitudinal axis of said image forming means passing through said target-focus zone.

4. The apparatus of claim 1, wherein said connecting means further comprises means for rotating said image forming means about its longitudinal axis.

5. The apparatus of claim 1, wherein said generator comprises focusing means for focusing the generated waves to an external focus constituting said target-focus zone, said focusing means being filled with a coupling liquid.

6. The apparatus of claim 5, wherein said image forming means comprises an ultrasonic transducer.

7. An apparatus for real-time tracking and imaging of an object present within the body of a mammal, said apparatus comprising:

a wave generator generating waves adapted to effect appropriate treatment of said object and directed towards a target-focus zone put into coincidence with said object;

image forming means forming a real-time image of said object for real-time observation of the latter; and means for connecting said image forming means with said wave generator, said connecting means including means for displacing said image forming means in a displacement plane coinciding with a symmetry plane of said generator including said target-focus zone and including a longitudinal axis of said image forming means, said image forming means being coupled to said displacing means whereby said image forming means is movable in said displacement plane relative to said target-focus zone, wherein said displacing means further comprises means for displacing said image forming means from one peripheral point on said wave generator to another peripheral point thereon.

8. An apparatus for real-time tracking and imaging of a concretion in a cavity of a mammal for destruction of said concretion into fragments that can be evacuated by natural passages, said apparatus comprising:

a pressure wave generator generating pressure waves directed towards a target-focus zone put into coincidence with said concretion;

image forming means for forming a real-time image of said concretion for real-time observation of the latter; and means for connecting said image forming means with said pressure wave generator, said connecting means including means for displacing said image forming means in a displacement plane coinciding with a symmetry plane of said generator containing said target-focus zone and containing a longitudinal axis of said image forming means, said image forming means being coupled to said displacing means whereby said image forming means is movable in said displacement plane relative to said target-focus zone, wherein said connecting means further comprise second means mounted to said generator for displacing said image forming means from one peripheral point on said generator to another peripheral point on said generator.

9. The apparatus of claim 8, wherein said displacing means comprises means for moving said image forming means in translation along said longitudinal axis of said image forming means passing through said target-focus zone.

10. The apparatus of claim 9, wherein said displacing means comprises means for rotating said image forming means within said displacement plane around said target-focus zone.

11. The apparatus of claim 8, wherein said displacing means comprises means for rotating said image forming means within said displacement plane around said target-focus zone.

12. An apparatus for real-time tracking and imaging of an object within the body of a mammal for treatment of said object, said apparatus comprising:

a wave generator generating waves directed towards a target-focus zone put into coincidence with said object;

image forming means forming a real-time image of said object for real-time observation of the latter; and means for connecting said image forming means with said wave generator, said connecting means including means mounted on said generator for displacing said image forming means from one peripheral point on said generator to another peripheral point on said generator, said displacing means comprising a rail type coupling system including a rail portion fixed to said generator and a displaceable portion movably mounted relative to said fixed rail portion, said image forming means being linked to said displaceable portion.

13. The apparatus of claim 12, wherein said connecting means further comprises second means for displacing said image forming means in a displacement plane coinciding with a symmetry plane of said generator including said target-focus zone and including a longitudinal axis of said image forming means, said image forming means being coupled to said displacing means whereby said image forming means is moveable in displacement in said displacement plane relative to said target-focus zone.

14. An apparatus for real-time tracking and imaging of an object within the body of a mammal to perform treatment of said object, comprising a wave generator generating waves directed towards a target-focus zone put into coincidence with said object, image forming means forming a real-time image of said object for real-time observation of the latter, and means for connecting said image forming means with said wave generator, said connecting means comprising means for displacing said image forming means in a displacement plane coinciding with a symmetry plane of said generator including said target-focus zone and a longitudinal axis of said image forming means, said displacing means comprising displacement measuring means for measuring the distance of displacement of the displacing means, whereby said image forming means is movable in displacement relative to said target-focus zone and the displacement distance may be determined.

15. An apparatus for real-time tracking and imaging of an object present within the body of a mammal, said apparatus comprising;
a wave generator generating waves adapted to effect appropriate treatment of said object and directed towards a target-focus zone put into coincidence with said object;
image forming means forming a real-time image of said object for real-time observation of the latter; and
means for connecting said image forming means with said wave generator, said connecting means including means for displacing said image forming means in a displacement plane coinciding with a symmetry plane of said generator including said target focus zone and including a longitudinal axis of said image forming means, said image forming means being coupled to said displacing means whereby said image forming means is movable in said displacement plane relative to said target-focus zone, wherein said displacing means comprises means for rotating said image forming means within said displacement plane around said target-focus zone, wherein said displacing means further comprises means for displacing said image forming means from one peripheral point on said wave generator to another peripheral point thereon.

16. An apparatus for real-time tracking and imaging of an object present within the body of a mammal, said apparatus comprising:
a wave generator defining a longitudinal axis for generating waves adapted to effect appropriate treatment of said object and directed towards a target-focus zone put into coincidence with said object;
image forming means forming a real-time image of said object for real-time observation of the latter; and
means for connecting said image forming means with said wave generator, said connecting means including means for displacing said image forming means in a displacement plane coinciding with a symmetry plane of said generator including said target-focus zone and including a longitudinal axis of said image forming means, said image forming means being coupled to said displacing means whereby said image forming means is movable in said displacement plane relative to said target-focus zone, wherein, in its usual working position, the longitudinal axis of said image forming means subtends an angle of approximately 45° with respect to said longitudinal axis of said wave generator.

* * * * *